United States Patent [19]
Selby et al.

[11] Patent Number: 6,083,380
[45] Date of Patent: Jul. 4, 2000

[54] FLUID COALESCING METHOD AND APPARATUS

[75] Inventors: Theodore W. Selby, Midland; Andrew J. Stephenson, Bay City, both of Mich.

[73] Assignee: Tannas Co., Midland, Mich.

[21] Appl. No.: 08/425,588

[22] Filed: Apr. 20, 1995

[51] Int. Cl.$^7$ .............................. C10G 5/00; B01L 11/00; B01D 3/00

[52] U.S. Cl. ......................... 208/340; 208/368; 585/921; 585/922; 202/185.1; 202/185.3; 202/268; 203/DIG. 2; 422/101; 165/913

[58] Field of Search .................... 208/340, 368; 422/101; 202/185.1, 185.3, 185.5, 268; 585/921, 922; 203/DIG. 2; 165/913

[56] References Cited

U.S. PATENT DOCUMENTS

| | | | |
|---|---|---|---|
| 2,116,442 | 5/1938 | McCluer | 422/101 X |
| 3,484,077 | 12/1969 | Porter | 422/103 X |
| 3,490,736 | 1/1970 | Snyder | 422/103 X |
| 3,864,214 | 2/1975 | Ohakas | 202/186 |
| 4,259,293 | 3/1981 | Najarian et al. | 422/109 |
| 4,437,937 | 3/1984 | McGraw | 202/160 |
| 4,689,237 | 8/1987 | Fabre | 426/521 |
| 5,061,300 | 10/1991 | Alexander, III | 55/30 |
| 5,242,643 | 9/1993 | Kim et al. | 422/129 |
| 5,667,302 | 9/1997 | Selby et al. | 374/54 |
| 5,692,832 | 12/1997 | Selby | 374/54 |

OTHER PUBLICATIONS

Selby, U.S. Patent application 08/773342, Dec. 26, 1996.
Selby et al., U.S. application 08/893632, Jul. 11, 1997.
Selby et al., U.S. Patent application 29/085603, Mar. 26, 1998.
Zumdahl, "Chemistry", D. C. Heath and Co., pp. 25 and 26, 1989.
Van Nostrand's Scientific Encyclopedia, Eighth edition, pp. 857 and 858, Feb. 1995.
Parker Filtration Bulletin 1300–700/NA, The Basics of Coalescing Filtration, ca. 1991–1992.
Peters et al., *Chemical Separation and Measurements*, W.B. Saunders Co., Philadelphia, Pa., 1974, pp. 480–481.
JPI–55–41–93 (1993).
CEC L–40–T–87 (1987).
Roberts et al., "An Introduction to Modern Experimental Organic Chemistry." 2nd Edition, Holt,Rinehart and Winton, Inc., New York, 1974, p. 36.
Rudy, "Cobalt (III) Complexes with (R)–1,2–Diaminopropose and Its Derivatives," W. Mich. U., M.A., 1985, University Microfilms, Ann Arbor, pp. 32–33.
AceGlass, Inc., Catalog 1200, Vineland, N.J., 1992, pp. 281–284, 353 & 382.
Cole–Parmer Instrument Co., 1993–1994 Catalog, Niles, Ill., pp. 414–415.
Hydrick, *Lubricants World*, vol. 4, No. 12, Dec. 1994, pp. 7, 10–11 & 14.
Roberts et al., "An Introduction to Modern Experimental Organic Chemistry," Second Edition, Holt, Rinehart and Winston, Inc., New York, 1974, back plate.
Schloemann, "Modified Noack Volatility Studies," ASTM Committee D02.06.B/04.L; Atlanta, Ga., Dec. 1994.
Selby, "The Problems and the Opportunities in the Use and Reuse of Lubricating Oils to Meet the Needs of Modern Engines," 1994.
Selby et al., "A New Approach to the Noack Volatility Test," Jan. 1994.
Selby et al., "Base Oil Characterization Techniques Using a New Approach to the Noack Volatility Test," 1994.

*Primary Examiner*—Walter D. Griffin
*Attorney, Agent, or Firm*—Christopher John Rudy

[57] ABSTRACT

A method to condense or coalesce matter is carried out by providing a suitable, narrow passageway for throughput of matter in a vapor state, and passing the matter in a vapor state through said passageway, under conditions such that the matter is coalesced into a more ordered state. Also, a matter coalescing apparatus has a hollow housing in communication with at least one of—(A) a plurality of suitably narrow hollow passageways and (B) a suitably narrow, elongately hollow, matter-coalescing passageway—for throughput of matter to include as a vapor therein. Consequently, highly efficient yields of coalesced matter, to include liquid coalesced from vapor, even under only mild vacuum or at about ambient atmospheric pressure can be obtained. This is especially so with respect to oils, where yields as high as 95 percent or greater can be provided hereby. The invention can be practiced under such outstanding yield efficiencies without a general need for significant external cooling.

20 Claims, 1 Drawing Sheet

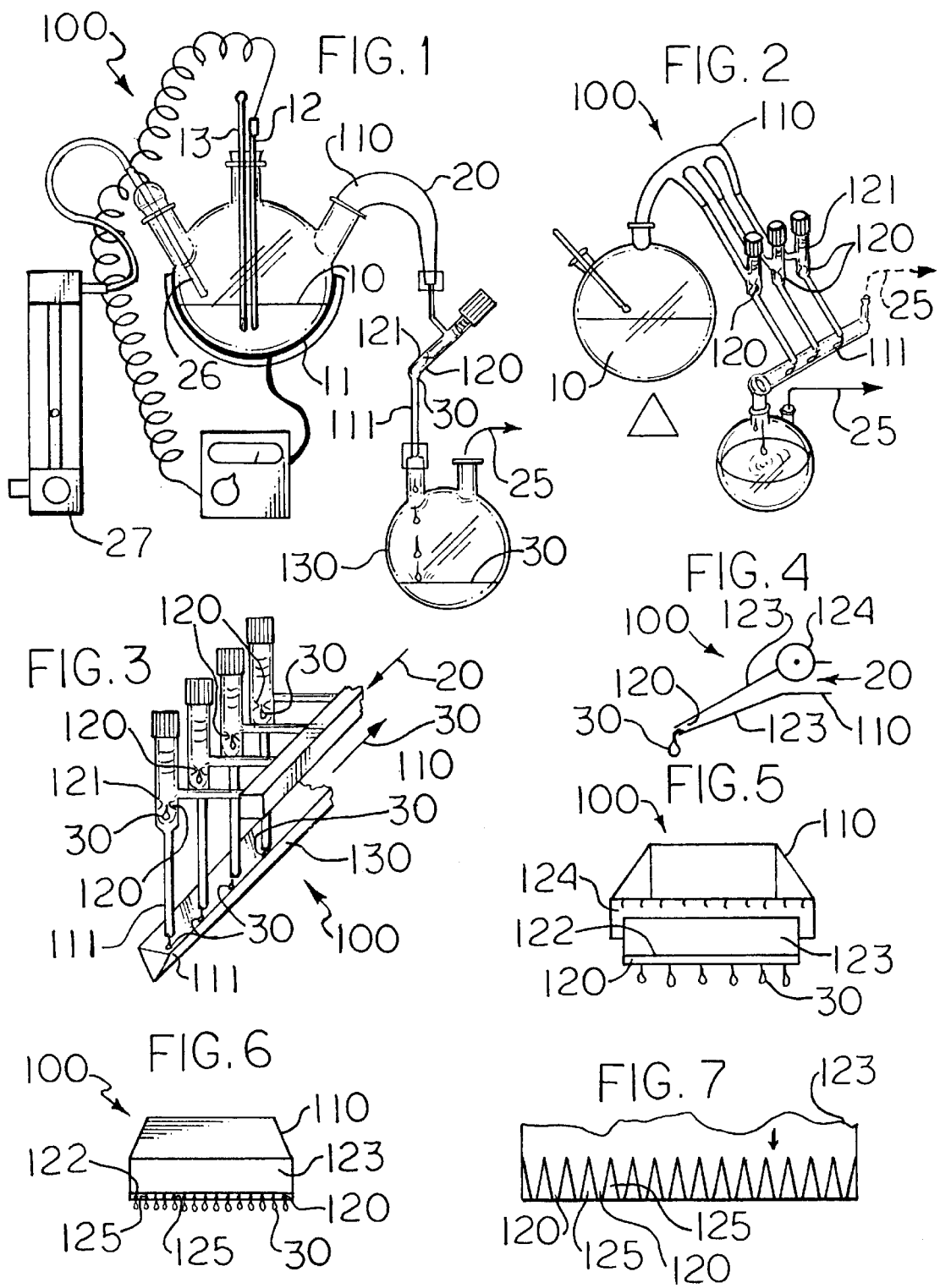

FLUID COALESCING METHOD AND APPARATUS

FIELD

The present invention concerns coalescing of matter.

BACKGROUND

Known methods at about atmospheric pressure to condense fluids from a vapor to the liquid phase typically involve condensers and externally applied cooling thereof to condense the fluid as a liquid. A number of modifications include use of theoretical plate increasing apparatus such as baffles or beads, for example, as in Hempel fractionating columns, Vigreux columns, glass packed columns, and so forth. In commercial practice, very low pressure (very high vacuum) methods are employed generally at high yields.

However, attempts to condense or coalesce oils at ambient pressure or even low or so-called mild vacuum with such apparatus and methodology can be highly problematical. The cooling of condensers such as by water, ice, dry ice, liquid nitrogen and so forth can be energy inefficient and even expensive. Moreover, such ambient pressure and mild vacuum methodology can be highly inefficient in yield of liquid from the vapor phase, especially with respect to oils. For example, in the lab, with typical motor oils, in an ambient pressure or mild vacuum method, the yield of condensed liquid from the vapor phase is often as low as 5 percent of theory; improvements in the yield, up to about 15 percent of theory, are possible the employment of glass bead packed condensers, and up to about 80 percent of theory are obtainable with dry ice cooling. Yet, such ambient pressure and mild vacuum methods can damage the fluid. In the case of commercially practiced very high vacuum methodology, yields of oils, for example, can reach or exceed 90 percent of theory, but a relatively great energy input is required to heat the sample, provide the very high vacuum, and so forth, which may also be inefficient. Such inefficiencies are undesirable.

In the lubricant art, an historical view of the needs in the art reveals pertinent factors, to include as follows:

1) Volatility measurements are important to lubricant function determination, to include, for example, a phosphorus loss effect on emissions by a poisoning of the catalyst of vehicle catalytic converters.

2) Hence, tests such as the Noack test are employed. Therein, weight loss is measured by difference in pot liquid before and after sample volatilization.

3) Since, in the Noack test, the volatilized fluid is not collected, an ability to analyze that fraction of volatilized fluid is generally lost except with gas chromatography, which is often not well suited to effective analysis of the copious fluid amount.

What is lacking and needed in the art are efficient yields of condensed liquid from vapor. This is especially so with respect to oils, and in the lubricant testing art.

SUMMARY

The present invention provides, in one aspect, a method to coalesce matter comprising providing a suitable, narrow passageway for throughput of matter in a vapor state, and passing the matter in a vapor state through said passageway, under conditions such that the matter is coalesced into a more ordered state. As well, provided is an apparatus useful for coalescing of matter comprising a hollow housing in communication with at least one of—(A) a plurality of suitably narrow hollow passageways, and (B) a suitably narrow, elongately hollow, matter-coalescing passageway—for throughput of matter to include as a vapor therein.

The invention is useful in matter coalescing.

The invention provides for highly efficient yields of coalesced matter, to include liquid coalesced from vapor, even under only mild vacuum or at about ambient atmospheric pressure. This is especially so with respect to oils, where yields as high as 95 percent or greater can be provided hereby. Of great significance as well, the invention can operate under such outstanding yield efficiencies without a general need for significant external cooling.

Numerous further advantages attend the invention.

DRAWINGS

The drawings form part of the specification hereof. In the drawings, where like numerals refer to like features, in general, note the following brief description:

FIG. 1 is a general side view of an apparatus employed in practice of the present invention.

FIG. 2 is a general side view of an apparatus embodiment of the invention.

FIG. 3 is a general side view of another embodiment of the invention.

FIG. 4 is side cut away view of yet another embodiment of the invention.

FIG. 5 is a front view of the apparatus as of FIG. 4.

FIG. 6 is a front view of a further embodiment hereof.

FIG. 7 is a top cut away view of part of the apparatus embodiment as of FIG. 6.

ILLUSTRATIVE DETAIL

In general herein, the term "coalesce" includes not only the union of two or more droplets of a liquid to form a larger droplet, brought about when the droplets approach one another closely enough to overcome their individual surface tensions, but also, both an analogous situation in the case of solids, should that occur, plus standard condensation, i.e., the change of state of a substance from the vapor to the liquid or to the solid form. Also, it may include a change in state of a substance from the vapor state to another more ordered state than the vapor state, for example, to a supercritical fluid state. The term "matter" includes a substance in a vapor, liquid, solid and/or a supercritical state, to include as an aerosol, smoke, etc.

With present invention, matter can be coalesced.

The present method requires as a minimum only one suitable, narrow passageway for throughput of the matter in a vapor state. However, a plurality of such passageways may be employed. The matter is passed in a vapor state through the passageway(s). Conditions are those such that the matter is coalesced into a more ordered state therewith.

Preferably, the passageway has a constriction therein, and the matter is coalesced proximate the constriction. As an example, a passageway constriction from that approaching 0 to about 5 to 8 mm may be advantageously employed.

Preferably, the passageway is positioned in a manner so as to provide for the passage of effluent vapor thereunder. Thus, the coalesced vapor can be directed downwardly so as to not back up and clog the passage of the matter in a vapor phase to and through the passageway and/or any constriction.

As the matter, any substance which can be coalesced by the practice of the invention may be employed. Preferably, the more ordered state is the liquid state. The invention is especially suitable for the coalescence of matter which includes oleaginous matter. Accordingly, oils, to include petroleum based motor oils, are advantageously coalesced in with the practice of the invention. The oil may be of a mixture of compounds, as with 300 to 400 molecular weight motor oil, or be composed of one compound, as with cetane. For example, virtually hundreds of motor oils can be most efficiently coalesced by employing the method of the invention. So-called synthetic motor oils may be employed to advantage herein also.

Temperatures of the method are any which can provide for the coalescence of the matter, and generally are about that of the vapor phase. Also, a pertinent temperature is that which is sufficient to establish the matter in the vapor state. Of course, the temperature should not be so high that the more ordered state may not form as desired.

One great advantage of the invention is that external cooling is not typically required such as provided by blowing air, water jackets, other cooling baths, etc. Thus, forced cool air, water, ice, salt in ice, dry ice slushes, liquid nitrogen, etc., cooling is not typically required and preferably is absent, especially about the suitable, narrow passageway, to effect the coalescence. Any vapor cooling as by ambient air is not considered to be external cooling.

Pressures of the method include any pressure which can provide for the coalescence. Advantageously, low to mild vacuum sub-atmospheric to ambient pressures such as from about 0.1 to about 800 mmHg can be employed. In general, a low vacuum is from about 0.1 to 10 mmHg, and a mild vacuum is above about 10 mmHg to below atmospheric pressure. Higher pressures may be employed as the situation would dictate. A range of subatmospheric internal system pressure desirable herein may be about from 0.5 to 500 mmHg.

The matter in the vapor state may be passed through the suitable, narrow passageway(s) and/or constriction(s) by pulling it with the application of reduced pressure to the system after the passageway and/or constriction. Alternatively, the matter may be passed therethrough by pushing it with the application of increased pressure to the system before the passageway(s) and/or constriction(s). As a further alternative, the matter may be passed therethrough with pressure from the generation of vapor as in a closed system save passageway(s) and/or constriction(s). Pulling as by application of a vacuum with a flow of air generated by the vacuum is preferred to especially include in testing.

The present apparatus has a hollow housing in communication with (A) a plurality of suitably narrow, hollow passageways, or (B) a suitably narrow, elongately hollow, matter-coalescing passageway, or at least one of the former (A) with one or more of the latter (B). The housing and required passageway(s) are for the throughput of matter to include as a vapor therein. Preferably, the required passageway(s) have at least one matter-coalescing, to include fluid-coalescing, constriction therein.

The housing, narrow passageway and/or constriction can be made of any suitable material. Materials generally chemically inert to the fluid passing through are preferred for making the passageway. For example, the passageway can be made in general of glass, inert plastic and/or metal such as brass or stainless steel. With oils, materials which are inert to components in the test oil, or materials which would not interfere or react with the test oil or later employed catalysts such as oil hydrogenation catalysts, generally such as glass, Teflon, etc., are preferred.

In reference to the not necessarily limiting embodiments depicted in the drawings, apparatus 100 has hollow, generally imperforate, housing 110 for throughput of matter therein. In general, it has at least one suitably narrow portion, or preferably a constriction 120, therein.

For example, as depicted in oil testing methodology apparatus, pot liquid 10 may be heated to provide vapor 20. A noble metal electric heater 11, controlled with thermocouple 12 and monitored by thermometer 13, heats the pot liquid 10.

The passageway is generally suitable for the throughput of the fluid in a vapor state 20. The passageway can be of a tubular, other hollow shape, or combination thereof.

As can be seen in the drawings, the housing/passageway 110 and constriction 120 can be unobstructed.

The passageway can take any shape which is conducive to the coalescence of matter from the vapor state, for example, fluid coalescence where vapor is coalesced into liquid 30, by the practice of the invention.

The passageway, accordingly, can include a generally annular constriction 121 such as provided by a needle valve, for example, threaded vacuum stopcock with Teflon plug that permits adjustment down to 0.1 cc/minute flow rate with an in-line arrangement of its barrel which has a constriction orifice size of from approaching 0 to about 3 mm, as with the well known model 8192-202 Low Hold-Up, Teflon, vacuum stopcock commercially available from Ace Glass, Inc., Vineland, N.J., as depicted within FIGS. 1 & 2. The generally annular constriction may be provided by a needle valve, for example, threaded vacuum stopcock with Teflon plug that permits adjustment down to 0.1 cc/minute flow rate with a 90-degree arrangement of its barrel which has a constriction orifice size of from approaching 0 to about 3 mm, as with the well known model 8193-214 Teflon, vacuum, needle valve stopcock commercially available from Ace Glass, Inc., as depicted within FIG. 3.

The passageway may be the suitably narrow, elongately hollow, matter-coalescing passageway. Illustrations of this construction are depicted in FIGS. 4–7, where a laterally extending constriction 122 such as provided by plates 123 close from a larger to a smaller volume. The laterally extending constriction 122 may movable as about pivot 124 and/or be divided with longitudinally spaced baffles 125. Preferably, the opening at the constriction closes to nearly 0 to about 3 to 8 mm, especially 3 mm or less.

The matter may be pulled as by application of a vacuum 25. A flow of air generated by the vacuum is drawn through air tube 26, monitored by flowmeter 27, for example, a valve containing 150-mm variable area flowmeter as commercially available from Cole-Parmer Instrument Co., Chicago, Ill.

In general, after the constriction, the passageway may end or continue for length 111 with relatively unconstricted flow therethrough permitted. Constrictions may be present in series, i.e., e.g., one after another, or may be present in a parallel fashion, i.e., e.g., side by side. A solitary constriction may be sufficient to provide marked yields.

Vessel 130 may be employed to collect the condensed liquid 30. The vessel is generally constructed of materials similar to the housing, passageway and/or constriction so as to be inert to its contents.

Practice of the present invention can provide highly efficient yields of liquid condensed from vapor. Thus, yields of liquid from the vapor can be about 30 percent of theory or greater, to include about 50 percent of theory or greater, 80 percent of theory or greater, or 90 percent of theory or greater, to include with oils. Highly efficient yields are especially noticed with respect to oils, where efficiencies as high as about 95 percent or greater can be provided hereby.

Again, the invention can operate under such outstanding yield efficiencies without a general need for significant external cooling. This is a most significant property of the invention. As well, oils are often not damaged hereby.

It is well worth noting that, in testing, for example, in the usual Noack test with more vapor throughput, less volatiles are collected. Most surprisingly, however, with the practice of the present invention, as under an improved Noack type test protocol, with the more throughput, more volatiles are collected.

The following examples further illustrate the invention. Therein, parts and percentages are by weight.

EXAMPLE 1

The glassware apparatus of FIG. 1 is cleaned, dried, and tared. A reference standard Noack oil sample, 65.01 g, is added to the three-necked flask, which is enveloped by a glass-fused noble metal heater, and the apparatus is assembled, using a light coating of high temperature hydrocarbon grease at the joints and at O-rings of the Ace Code 8194-202 needle valve. The thermometer and thermocouple are placed about 3/16-inch (ca. 0.44 cm) from the bottom of the flask. The flow control valve is closed, and the unit is heated so that the temperature of the pot liquid is 250 degrees C. At that point and at 30.02 inches of mercury (762.3 mmHg) external air pressure, a pump applies a vacuum beyond the collection flask, the flow control valve is opened, and the internal pressure is adjusted by the manometer to 12 mm water (0.8826, i.e., 0.88 mmHg). Air flow is about 2723 mL/minute. At 5 minutes, the vacuum is turned off, and next, the heaters. The percent (%) of the sample which is volatilized is 15.81 (compared to a 15.6% standard Noack reference value). The pot loss is 10.28 g, and 9.61 g of the sample is collected, yielding 93.48%.

EXAMPLE 2

The protocol of Example 1 is repeated at 30.02 inches of mercury (762.3 mmHg) using 65.01 g of a motor oil as the sample material. The pot loss is 12.59 g, and 11.14 g of the volatilized sample is collected, for a yield of 88.48%.

EXAMPLE 3

The protocol of Example 1 is repeated at 30.02 inches of mercury (762.3 mmHg) using 65.01 g of a motor oil as the sample material. The pot loss is 15.30 g, and 13.80 g of the volatilized sample is collected, for a yield of 90.20%.

EXAMPLE 4

The protocol of Example 1 is repeated at 30.13 inches of mercury (762.3 mmHg) using 65.00 g of a motor oil as the sample material. The pot loss is 12.67 g, and 11.92 g of the volatilized sample is collected, for a yield of 94.08%.

EXAMPLE 5

The protocol of Example 1 is repeated at 30.13 inches of mercury (762.3 mmHg) using 65.00 g of a motor oil as the sample material. The pot loss is 19.77 g, and 18.94 g of the volatilized sample is collected, for a yield of 95.80%.

EXAMPLE 6

The protocol of Example 1 is repeated at 30.13 inches of mercury (762.3 mmHg) using 65.00 g of a motor oil as the sample material. The pot loss is 18.93 g, and 18.32 g of the volatilized sample is collected, for a yield of 96.78%.

CONCLUSION

The present invention is thus provided. Numerous modifications can be effected within its spirit, the literal claim scope of which is particularly pointed out as follows:

We claim:

1. A method to coalesce oleaginous matter comprising providing a suitable, unobstructed, narrow passageway for throughout of oleaginous matter in a vapor state, and passing the matter in a vapor state through said passageway, under conditions such that the matter is coalesced into a more ordered state, wherein external cooling is not employed, wherein said passageway has a constriction therein, and the oleaginous matter is passed in the vapor state through said passageway and said constriction, under conditions such that the oleaginous matter is coalesced into a more ordered state proximate said constriction.

2. The method of claim 1, wherein the more ordered state is a liquid state.

3. The method of claim 2, wherein the oleaginous matter is an oil.

4. The method of claim 1, which is conducted at a pressure of about 0.1 to 800 mm Hg, and wherein yield of said matter is at least about 90 percent of theory by weight.

5. The method of claim 2, which is conducted at a pressure of about 0.1 to 800 mm Hg, and wherein yield of said matter is at least about 90 percent of theory by weight.

6. The method of claim 3, which is conducted at a pressure of about 0.1 to 800 mm Hg, and wherein yield of said matter is at least about 90 percent of theory by weight.

7. The method of claim 1, which is conducted at a pressure of about 0.1 to 800 mm Hg, wherein the more ordered state is a liquid state; wherein the oleaginous matter is a motor oil, and wherein yield of said matter is at least about 95 percent of theory by weight.

8. A method to coalesce matter comprising providing a suitable, unobstructed, narrow passageway for throughput of matter in a vapor state, said passageway having a constriction therein; and passing the matter in the vapor state through said passageway and said constriction, under conditions such that the matter is coalesced into a more ordered state proximate said constriction, wherein external cooling is not employed.

9. The method of claim 8, wherein yield of said matter is at least about 50 percent of theory by weight.

10. The method of claim 9, wherein said more ordered state is a liquid state, and which is conducted at a pressure of about 0.1 to 800 mm Hg, and wherein yield of said matter is at least about 90 percent of theory by weight.

11. The method of claim 8, with the yield at least about 95 percent of theory by weight.

12. The method of claim 10, with the yield at least about 95 percent of theory by weight.

13. A method to coalesce oleaginous matter comprising providing a suitable, unobstructed, narrow passageway for throughput of oleaginous matter in a vapor state, and passing the matter in a vapor state through said passageway, under conditions such that the matter is coalesced into a more ordered state, wherein external cooling is not employed, wherein said passageway has a constriction therein, and the oleaginous matter is passed in the vapor state through said passageway and said constriction, under conditions such that the oleaginous matter is coalesced into a more ordered state proximate said constriction, and wherein said passageway is positioned in a manner such that the coalesced vapor can be directed downwardly so as to not back up and clog the passage of the matter in the vapor state to and through said passageway and said constriction.

14. The method of claim 13, wherein the oleaginous matter is an oil.

15. The method of claim 14, wherein the oil is a motor oil.

16. The method of claim 13, wherein yield of said oleaginous matter is at least about 90 percent of theory by weight.

17. The method of claim 14, wherein yield of said oil is at least about 90 percent of theory by weight.

18. The method of claim 15, wherein yield of said motor oil is at least about 90 percent of theory by weight.

19. The method of claim 14, wherein yield of said oil is at least about 95 percent of theory by weight.

20. The method of claim 15, wherein yield of said motor oil is at least about 95 percent of theory by weight.

* * * * *